200
United States Patent [19]

Schamper et al.

[11] Patent Number: 4,725,430

[45] Date of Patent: Feb. 16, 1988

[54] ACID STABLE DIBENZYL MONOSORBITOL ACETAL GELS

[75] Inventors: Thomas J. Schamper, Ramsey, N.J.; Martin M. Perl, Brooklyn; James D. Warren, Pearl River, both of N.Y.

[73] Assignee: American Cyanamid Company, Stamford, Conn.

[21] Appl. No.: 776,984

[22] Filed: Sep. 13, 1985

Related U.S. Application Data

[63] Continuation of Ser. No. 596,074, Apr. 3, 1984, abandoned, which is a continuation of Ser. No. 348,578, Feb. 12, 1982, abandoned.

[51] Int. Cl.$^4$ .......................... A61K 7/32; A61K 7/34; A61K 7/38
[52] U.S. Cl. .............................. 424/66; 424/DIG. 5; 424/68
[58] Field of Search ...................... 424/68, DIG. 5, 66

[56] References Cited

U.S. PATENT DOCUMENTS

| 4,265,878 | 5/1981 | Keil | 424/68 |
| 4,346,079 | 8/1982 | Roehl | 426/DIG. 5 |

FOREIGN PATENT DOCUMENTS

| 1344224 | 10/1963 | France | 424/65 |
| 1365793 | 5/1964 | France | 424/65 |
| 48-9984 | 2/1973 | Japan | 424/65 |
| 51-19114 | 2/1976 | Japan | 424/65 |

OTHER PUBLICATIONS

Martindale, The Extra Pharmacopoeia 7/1958, vol. I, pp. 1231,1232,1343 and 1348.

Primary Examiner—Dale R. Ore
Attorney, Agent, or Firm—C. J. Fickey

[57] ABSTRACT

A clear or translucent cosmetic stick containing an acidic material and a reactive solvent, using dibenzyl monosorbitol acetal as the gelling agent an N-(2-hydroxyethyl) acetamide as the stabilizing agent. In particular are included antiperspirant sticks with an astringent metal salt and also containing lower aliphatic mono- and dihydric alkanols.

6 Claims, No Drawings

ACID STABLE DIBENZYL MONOSORBITOL ACETAL GELS

This application is a continuation of application Ser. No. 596,074, filed, Apr. 3, 1984, which is a continuation of Ser. No. 348,578, filed Feb. 12, 1982, both abandoned.

The present invention relates to gelled cosmetic sticks in general. More particularly, it relates to gelled antiperspirant sticks containing an acidic antiperspirant-active compound. Still more particularly, it relates to antiperspirant sticks containing an acidic antiperspirant-active compound in the presence of dibenzyl monosorbitol acetal (DBMSA) as the gelling agent, and to a method for the stabilization of said sticks against deterioration.

Many known cosmetic sticks consist largely of gelled alcoholic solutions. Sticks which exhibit a desirable transparent or translucent appearance are readily prepared using sodium stearate as the gelling agent; however, they cannot be prepared in the presence of acidic antiperspirant-active salts because the alkaline gelling agent will react with the salt. Opaque sticks are readily prepared from acidic antiperspirant salts using certain low melting waxy materials, such as stearyl alcohol. The sticks are stable, but there is a need for a method of making acid-stable, translucent antiperspirant sticks, particularly using dibenzyl monosorbitol acetal as the gelling agent.

Dibenzyl monosorbitol acetal is a unique gelling agent, providing translucent sticks. No derivative of sorbitol or any other gelling agent has yet been found which provides sticks having equal properties. Dibenzyl monosorbitol acetal has been known for a long time. However, it is also known that acetals are stable in alkaline or neutral media, but not in acidic media. In an acidic environment, even in the presence of small amounts of water, the acetal hydrolyzes; or, it will react with a reactive alcohol, e.g. ethanol, to form a different acetal. Thus, antiperspirant sticks containing acidic antiperspirant-active compounds in the presence of dibenzyl monosorbitol acetal in reactive alcoholic solvents have not been satisfactory because, in time, especially at elevated temperatures, they deteriorate and liquify. There is a need, therefore, to find a way to stabilize these sticks against such deterioration.

Antiperspirant sticks containing dibenzyl monosorbitol acetal and acidic antiperspirant-active salts are disclosed by Roehl, U.S. Pat. No. 4,154,816 (Naarden). These sticks contain, in addition to the salt and gelling agent, a lower monohydric alcohol, such as ethanol; a di- or trihydric alcohol, such as 1,3-propylene glycol or 1,3-butylene glycol, and/or a lower polyglycol; a propylene-/ethylene glycol polycondensate, having the formula:

wherein $y/x+y=0.6-1$ and an average molecular weight of at least 500; and optionally, a mono- or dialkanlamide of a higher ($C_8$–$C_{20}$) fatty acid, such as N-(2-hydroxyethyl)cocamide.

In British application No. 2,062,466, Roehl discloses that a drawback to the sticks described above is their stickiness on application, which can be eliminated by entirely omitting, or greatly reducing, the polycondensate, and adding instead about 0 to 25 percent by weight of an oleaginous compound for stickiness control.

Applicants have found that the antiperspirant sticks described by Roehl are not stable on extended exposure at an elevated temperature.

In accordance with the present invention, antiperspirant sticks are provided containing dibenzyl monosorbitol acetal in the presence of acidic antiperspirant-active salts, which are stable for extended periods of time at elevated temperatures; said sticks comprising (a) about 1 to 80 percent by weight of at least one reactive solvent; (b) about 0 to 75 percent by weight of $C_3$ to $C_6$ secondary aliphatic monohydric alcohol or a $C_3$ to $C_6$ aliphatic dihydric alcohol; (c) about 1 to 10 percent by weight of dibenzyl monosorbitol acetal; (d) 0 to 25 percent of a cyclic dimethylsiloxane liquid; (e) about 5 to 25 percent by weight of an antiperspirant-active compound; (f) 0 to 2.5 percent by weight of a $C_{12}$–$C_{20}$ fatty acid; and (g) about 1 to 85 percent by weight of N-(2-hydroxyethyl)acetamide or combinations thereof with up to 5 percent by weight of N-(2-hydroxyethyl)cocamide, up to 1 percent by weight of magnesium sulfate, up to 1 percent by weight of zinc acetate, and up to 0.5 percent by weight of hexamethylenetetramine.

Reactive solvents include water, methanol, ethanol, n-propanol, n-butanol, 2-methoxyethanol, 2-ethoxyethanol; ethyleneglycol, 1,2-propylene glycol, 1,3-propylene glycol, 1,4-butylene glycol 1,2-butylene glycol, diethylene glycol, and the like, and mixtures thereof. Ethanol, because of its excellent solvent properties, is a preferred primary monohydric alcohol. However, since the primary alcohols, especially the lower alcohols are more reactive towards dibenzyl monosorbitol acetal in the presence of acid species, it is preferred that they be used in the least amount consistent with the preparation of satisfactory sticks. Generally it is preferred to use from about 5 to 65 percent by weight of these alcohols.

The $C_3$ to $C_6$ secondary aliphatic monohydric alcohols and $C_3$ to $C_6$ aliphatic dihydric alcohols are those which, because of the presence of less reactive secondary alcohol groups or because of their chain length, are less reactive towards dibenzyl monosorbitol acetal, include isopropanol, isobutanol, diethylene glycol monomethyl ether, diethylene glycol monoethyl ether; 1,3-butyleneglycol, 2,3-butylene glycol dipropylene glycol, 2,4-dihydroxy-2-methylpentane, and the like, and mixtures thereof. Preferred compounds are 1,3-butylene glycol and 2,4-dihydroxy-2-methylpentane. Because of their reduced reactivity towards dibenzyl monosorbitol acetal it is preferred to maximize their usage consistent with the preparation of satisfactory sticks. Generally, it is preferred to utilize from about 10 to 70 percent by weight of these alcohols.

A liquid volatile cyclic dimethylsiloxane may be added to the compositions to provide a dry feel and emolliency. Although optional, it is preferred to use from about 3 to 20 percent by weight.

The antiperspirant-active metal compounds useful in the present invention are the usual aluminum and/or zirconium compounds, especially aluminum hydroxy chlorides. They may be used in the form of a complex to enhance solubility in alcohols, such as aluminum chlorohydroxypropylene glycol or Al/Zr chlorohydrate propylene glycol. The metal salts are preferably used in an amount of about 10 to 20 percent by weight.

When solutions of aluminum hydroxy chlorides are heated there is a tendency towards premature gelation. This may be suppressed by the addition of a small amount of a $C_{12}$ to $C_{18}$ fatty acid, such as stearic acid, without adversely affecting the stability of the gel.

The stabilizer useful in the present invention to prevent or retard deterioration of the gelled sticks when exposed to elevated temperatures for prolonged periods of time is N-(2-hydroxyethyl)acetamide. Although alkylolamides of higher fatty acids, such as $C_8$ to $C_{24}$ fatty acids, have been reported to provide stability to the gels (See Roehl, British Application, Supra), it has been found that N-(2-hydroxyethyl)acetamide provides greater than twice the stability of, for example N-(2-hydroxyethyl)cocamide. The stabilizer may be used in an amount of about 1 to 85 percent by weight.

Additionally, it has been found that N-(2-hydroxyethyl)acetamide may be combined with one or more additional stabilizer compounds. Selected from magnesium sulfate, zinc acetate, hexamethylenetetramine and N-(2-hydroxyethyl)cocamide, to provide enhanced stability to the gels. The total stabilizer content of the gel, including combinations of N-(2-hydroxyethyl)acetamide, should not exceed about 85 percent by weight.

However, N-(2-hydroxyethyl)acetamide may be combined with up to 5 percent by weight of N-(2-hydroxyethyl)cocamide, up to 1 percent by weight of magnesium sulfate, up to 1 percent by weight of zinc acetate, and up to 0.5 percent by weight of hexamethylenetetramine. Combinations of N-(2-hydroxyethyl)acetamide with one or more of the additional stabilizers may be used. N-(2-hydroxyethyl)acetmide is preferably used alone. The amount of stabilizers used, other than the N-(2-hydroxyethyl)acetamide, should not exceed about 7.5 percent by weight.

In addition to the ingredients described about the antiperspirant sticks may contain a fragrance and a dye color if desired, and other ingredients in minor amount.

The following examples illustrate the invention.

Antiperspirant stick compositions were prepared as follows:

EXAMPLE 1

|  | Parts by Weight |
|---|---|
| Phase 1 | |
| 1,3-Butyleneglycol | 20.0 |
| Hexylene glycol | 10.0 |
| Steareth 100* | 1.0 |
| DBMSA | 3.0 |
| Phase 2 | |
| Stearic acid | 0.5 |
| Cyclomethicone | 5.0 |
| Ethanol (anhyd) | 50.3 |
| Aluminum Chlorohydrex | 10.0 |
| Hydroxypropyl cellulose | 0.2 |
| | 100.0 |

Phase 1 was heated to a clear solution at 100° C. and phase 2 was heated to a clear solution at 80° C. Phase 1 was added to phase 2, mixed briefly, poured into a mold and allowed to cool and gel. Sticks in the following Examples were prepared in a similar manner.

EXAMPLE 2

|  | Parts by Weight |
|---|---|
| 1,3-Butylene glycol | 25.0 |
| Hexylene glycol | 3.0 |
| Steareth 100 | 1.0 |
| DBMSA | 3.0 |
| Stearic acid | 0.5 |
| Cyclomethicone | 5.0 |
| Ethanol (anhyd.) | 42.3 |
| Aluminum chlorhydrex | 15.0 |
| Hydroxypropyl cellulose | 0.2 |
| Cocamide MEA | 5.0 |
| | 100.0 |

EXAMPLE 3

|  | Parts by Weight |
|---|---|
| 1,3-Butylene glycol | 25.0 |
| Hexylene glycol | 3.0 |
| Steareth 100 | 1.0 |
| DBMSA | 3.0 |
| Stearic acid | 0.5 |
| Cyclomethicone | 5.0 |
| Ethanol (anhyd.) | 42.3 |
| Aluminum chlorhydrex | 15.0 |
| Hydroxypropyl cellulose | 0.2 |
| Acetamide MEA | 5.0 |
| | 100.0 |

*Polyoxyethylene (100) stearyl alcohol.

The antiperspirant sticks prepared from the compositions of Examples 1–3 were exposed at a temperature of 45° C. and the time to deterioration (liquidity) was noted, as shown below.

|  | Time to Deterioration, Weeks |
|---|---|
| Product of Example 1 | 6 |
| Product of Example 2 | 12 |
| Product of Example 3 | >27 |

The stability data show that the product of Example 1, containing no stabilizer, deteriorates to a liquid after 6 weeks at 45° C. Cocamide MEA affords about a two-fold increase in stability and acetamide MEA (invention) is still stable after 27 weeks.

Examples 4 to 10 illustrate improvement in the stability of antiperspirant sticks by the use of acetamide MEA in combination with additional stick stabilizers. All parts are by weight.

| Ingredient | Example 4 | 5 | 6 | 7 | 8 | 9 | 10 |
|---|---|---|---|---|---|---|---|
| 1,3-Butylene glycol | 20.0 | 20.0 | 20.0 | 20.0 | 20.0 | 20.0 | 20.0 |
| Hexylene glycol | 10.0 | 10.0 | 10.0 | 10.0 | 10.0 | 10.0 | 10.0 |
| Steareth 100 | 1.0 | 1.0 | 1.0 | 1.0 | 1.0 | 1.0 | 1.0 |
| DBMSA | 3.0 | 3.0 | 3.0 | 3.0 | 3.0 | 3.0 | 3.0 |
| Stearic acid | 0.5 | 0.5 | 0.5 | 0.5 | 0.5 | 0.5 | 0.5 |
| Cyclic dimethyl siloxane | 5.0 | 5.0 | 5.0 | 5.0 | 5.0 | 5.0 | 5.0 |
| Ethanol(anhyd.) | 46.3 | 45.0 | 45.0 | 45.2 | 44.6 | 39.7 | 39.9 |
| Aluminum chlorohydrex | 10.0 | 10.0 | 10.0 | 10.0 | 10.0 | 10.0 | 10.0 |
| Hydroxypropyl cellulose | 0.2 | 0.2 | 0.2 | 0.2 | 0.2 | 0.2 | 0.2 |
| N—(2-hydroxyethyl)acetamide | 5.0 | 5.0 | 5.0 | 5.0 | 5.0 | 5.0 | 5.0 |
| N—(2-hydroxyethyl)cocamide | 5.0 | — | — | — | — | 5.0 | 5.0 |
| $MgSO_4$ | — | 0.3 | — | — | 0.3 | 0.3 | — |
| $Zn(O_2C_2H_3)_2$ | — | — | 0.3 | — | 0.3 | 0.3 | 0.3 |
| Hexamethylenetetramine | — | — | — | 0.1 | 0.1 | — | 0.1 |
| Stability at 60° C., days | >69 | 60 | >69 | >69 | >69 | >69 | >69 |

-continued

| | 11 | 12 | 13 |
|---|---|---|---|
| DBMSA | 3.0 | 3 | 4.5 |
| Hexylene Glycol | 20.00 | 23 | 20.00 |
| Butylene Glycol | 46.8 | 53.8 | 43.30 |
| Steareth 100 | — | — | — |
| Acetamide MEA | — | — | 2.0 |
| Aluminum chlorohydrex | 15.00 | 15.00 | 15.00 |
| Stearic Acid | — | — | — |
| Hydroxypropyl cellulose | 0.20 | .2 | 0.20 |
| Volatile silicone | 0.0 | — | — |
| Ethanol | 15.00 | 5 | 15.00 |
| | 100.00 | 100.00 | 100.00 |

Example 11, liquid in two days at 60° C.
Example 12, liquid in five days at 60° C.
Example 13, liquid in thirteen days at 60° C.

What is claimed is:

1. A solid transparent, gelled antiperspirant composition consisting essentially of:
   (a) 1 to 80% by weight of at least one reactive solvent selected from the group consisting of water and lower primary mono- and dihydric alcohols;
   (b) 0 to 75% by weight of a $C_3$ to $C_6$ secondary aliphatic monohydric or dihydric alcohol or mixture thereof;
   (c) 1 to 10% by weight of dibenzyl monosorbitol acetal;
   (d) 0 to 25% by weight of a volatile cyclic dimethylsiloxane liquid;
   (e) 5 to 25% by weight of an acidic antiperspirant-active metal salt;
   (f) 0 to 2.5% by weight of a $C_{12}$ to $C_{20}$ fatty acid; and
   (g) 1 to 85% by weight of a gel stabilizer; said gel stabilizer comprising N-(2-hydroxyethyl)acetamide, alone, or combined with one or more of magnesium sulfate, in an amount up to 1% by weight, zinc acetate, in an amount up to 1% by weight, N-(2-hydroxyethyl)cocamide, in an amount up to 5% by weight, and hexamethylenetetramine, in an amount up to 0.5% by weight.

2. A composition according to claim 1 wherein (a) is ethanol and (b) is 1,3-butylene glycol or 2,4-dihydroxy-5-methyl pentane, or a mixture thereof.

3. A composition according to claim 1 wherein the acidic antiperspirant-active metal salt is aluminum chlorohex.propylene glycol complex or aluminum/zirconium chlorohydrate.propylene glycol complex.

4. A compositon according to claims 1, 2, or 3 wherein said stabilizer is N-(2-hydroxyethyl)acetamide.

5. A solid, transparent gelled antiperspirant composition comprising:
   (a) 40 to 65% by weight ethanol;
   (b) 10 to 30% by weight of 1,3-butylene glycol or 2,4-dihydroxy-5-methyl pentane or a mixture thereof;
   (c) 2 to 10% by weight of dibenzyl monosorbitol acetal;
   (d) 5 to 20% by weight of a cyclic dimethylsiloxane liquid;
   (e) 10 to 15% by weight of an acidic antiperspirant-active metal salt;
   (f) 0.2 to 1% by weight of stearic acid; and
   (g) 2 to 10% by weight of N-(2-hydroxyethyl)acetamide.

6. A method for preventing the deterioration of a solid, gelled antiperspirant stick, consisting of an alcoholic solution of an acid antiperspirant-active metal salt and dibenzyl monosorbitol acetal, which comprises incorporating therein 1 to 85% by weight of a gel stabilizer consisting of N-(2-hydroxyethyl)acetamide, alone, or combined with one or more of magnesium sulfate, in an amount up to 1% by weight, zinc acetate, in an amount up to 1% by weight N-(2-hydroxyethyl)cocamide, in an amount up to 5% by weight, and hexamethylenetetramine, in an amount up to 0.5% by weight.

* * * * *